(12) United States Patent
Nakajima et al.

(10) Patent No.: US 7,408,633 B2  
(45) Date of Patent: Aug. 5, 2008

(54) APPARATUS AND METHOD FOR INSPECTING FILM DEFECT

(75) Inventors: Takeshi Nakajima, Kanagawa (JP); Manabu Higuchi, Kanagawa (JP); Takeshi Wakita, Kanagawa (JP)

(73) Assignee: FUJIFILM Corporation, Tokyo (JO)

( * ) Notice: Subject to any disclaimer, the term of this patent is extended or adjusted under 35 U.S.C. 154(b) by 260 days.

(21) Appl. No.: 11/359,567

(22) Filed: Feb. 23, 2006

(65) Prior Publication Data

US 2006/0203246 A1    Sep. 14, 2006

(30) Foreign Application Priority Data

Mar. 10, 2005    (JP) .............................. 2005-067747

(51) Int. Cl.
*G01N 21/00* (2006.01)

(52) U.S. Cl. ............... 356/237.2; 356/239.1; 356/239.7

(58) Field of Classification Search .... 356/237.1–241.6
See application file for complete search history.

(56) References Cited

U.S. PATENT DOCUMENTS

| | | | | |
|---|---|---|---|---|
| 4,972,091 A | * | 11/1990 | Cielo et al. ............ | 250/559.42 |
| 5,452,079 A | * | 9/1995 | Okugawa ................. | 356/239.1 |
| 5,691,811 A | * | 11/1997 | Kihira ...................... | 356/239.1 |
| 6,011,620 A | * | 1/2000 | Sites et al. ............... | 356/239.1 |
| 7,199,386 B2 | * | 4/2007 | Capaldo et al. .......... | 250/559.4 |

FOREIGN PATENT DOCUMENTS

| | | |
|---|---|---|
| JP | 6-148095 A | 5/1994 |
| JP | 6-235624 A | 8/1994 |
| JP | 8-54351 A | 2/1996 |
| JP | 9-73081 A | 3/1997 |
| JP | 11-30591 A | 2/1999 |

* cited by examiner

*Primary Examiner*—Gregory J. Toatley, Jr.
*Assistant Examiner*—Jarreas C Underwood
(74) *Attorney, Agent, or Firm*—Sughrue Mion, PLLC

(57) ABSTRACT

There is disclosed a defect inspection apparatus, wherein a light source projects a linear light onto a transparent film to inspect, so that a light receiver receives light beams transmitted through the film. The light receiver is placed to look down the film, with its optical axis inclined by a cross angle $\theta 1$ to a normal line that is perpendicular to the film surface, and the cross angle $\theta 1$ is set in a range from 30° to 50°. The optical axis of the light receiver is also turned about the normal line by a rotational angle $\theta 2$ to a transport direction (S) of the film. The rotational angle $\theta 2$ is set in a range from minus 60° to plus 60°, on the assumption that the transport direction is zero degree.

8 Claims, 5 Drawing Sheets

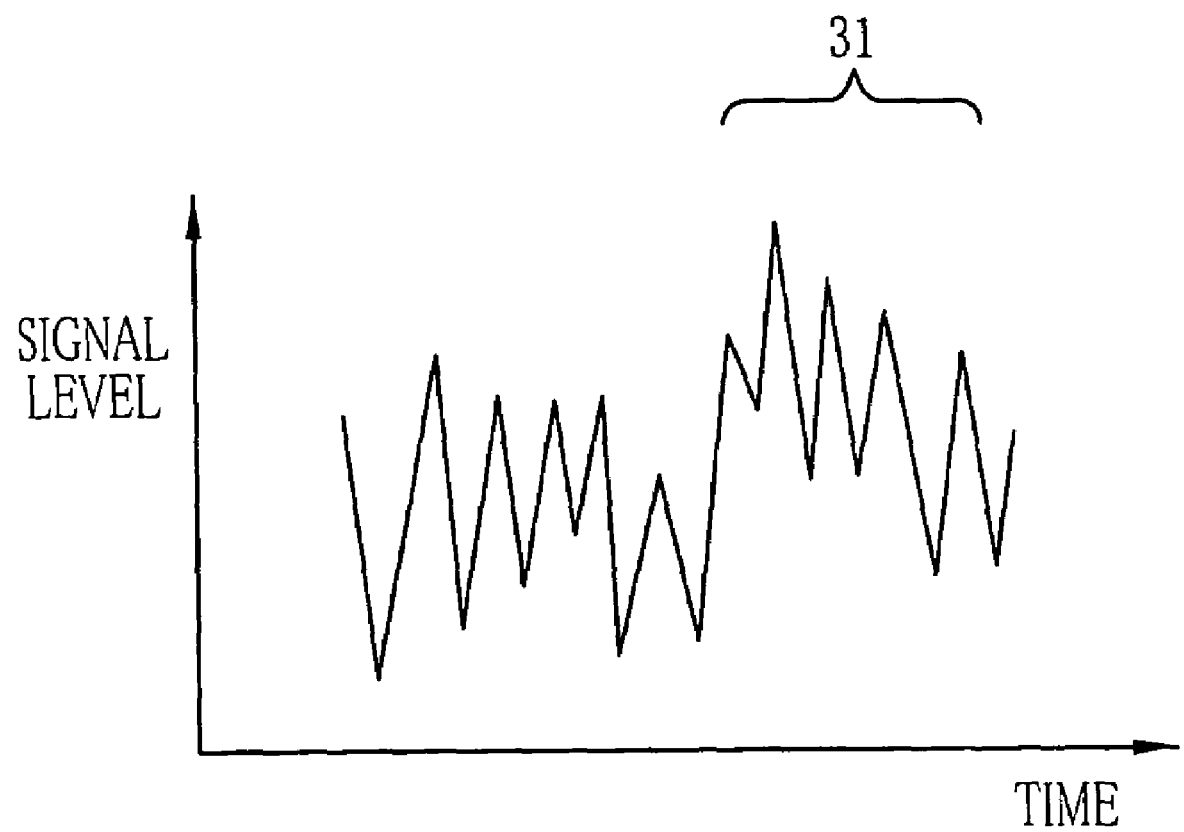

APPARATUS AND METHOD FOR INSPECTING FILM DEFECT

FIELD OF THE INVENTION

The present invention relates to a film detect inspection apparatus and a film defect inspection method, for inspecting defects of a film, such as uneven thickness, uneven coating, irregular molecular orientation of a liquid crystal layer, based on light transmitted through the film.

BACKGROUND ARTS

Optical compensation film, or retardation film, is known as a device for improving viewing angle of a liquid crystal display device. The optical compensation film is produced by forming an alignment film on a long web of transparent film, and then forming an optically anisotropic liquid crystal layer by spreading and drying a liquid crystal on the alignment film, as disclosed for example in Japanese Laid-open Patent Application No. Hei 9-73081. Although the manufacturing processes for the optical compensation film are strictly supervised, it is hard to exterminate any defect of the produced film. The film defect may be caused by various factors, like mixture or adhesion of extraneous matters, and includes irregularity of molecular orientation, uneven thickness of the base transparent film and uneven coating of the liquid crystal layer. For this reason, it is necessary to locate the detective position on the optical compensation film during the manufacture.

Defect inspection of the optical compensation film on the manufacturing line may be called the on-line inspection, and there are many conventional methods for the on-line inspection.

For example, Japanese Laid-open Patent Application No. Hei 6-235624 suggests an inspection method, wherein inspection light beams are projected from a light source toward a target transparent film as being conveyed, to receive reflected light beams or transmitted light beams on a linear sensor. Based on the received light beams, fine unevenness of the film surface, extraneous matters or air bubbles in the film, or protuberances produced on an antireflective coat on the film surface can be automatically detected at a high speed.

Japanese Laid-open Patent Application No. Hei 8-54351 discloses a defect inspection method, wherein a high-luminous high-directional light beam is projected at an angle of 5° to 15° onto a surface of a transparent sheet as being conveyed continually, and light transmitted through the transparent sheet is captured by a camera, so as to detect the film defect based on data obtained by image-processing an output signal from the camera. This method enables detecting fine unevenness of the film thickness, i.e. unevenness of 0.1 µm to 5 µm deep and 0.1 µm to 10 µm wide.

Japanese Laid-open Patent Application No. Hei 6-148095 discloses an inspection method, wherein a light source and a camera are placed in opposition to each other across a film to inspect, and a first polarizing plate is placed in front of the light source, whereas a second polarizing plate is placed in front of the camera. The film defect is detected based on data obtained by image-processing an output signal from the camera. Since the polarizing direction of the first and second polarizing plates is displaced by an angle of 20° or so from their vertical direction, it becomes possible to detect an increase in light intensity, which results from a change in polarizing condition, and occurs where an extraneous matter exits in or on the film.

Japanese Laid-open Patent Application No. Hei 11-30591 discloses a method, wherein a light source, a camera and first and second polarizing plates are arranged in the same way as in the above-mentioned Japanese Laid-open Patent Application No. Hei 6-148095, but the displacement of the polarizing direction of the polarizing plates is set to be not more than ±20°. Thereby, vertically polarized components, which are generated by irregular orientation of film molecular or fine distortion of the film, are reduced, so texture signals are lowered and local changes in transmitted light amount through the film are reduced. Then, a change in polarizing condition that occurs at a defective position is made apparent as a dark area signal.

However, any of the prior defect inspection methods cannot detect such a super fine defect that is measured as a thickness difference of 1 nm to 100 nm in film or coating thickness. The present applicant tried to detect uneven coating of a low reflective optical use film and an optical compensation film, using the inspection methods as disclosed in the above-mentioned Japanese Laid-open Patent Application Nos. Hei 6-235624 and Hei 8-54351. But it was hard to detect the super fine unevenness as above. Also with the prior art disclosed in the above-mentioned Japanese Laid-open Patent Application No. Hei 6-148095, satisfying results could not be obtained. Particularly, a change in polarizing direction that is caused by irregular molecular orientation or uneven thickness could not be detected in the vertical direction to the film, because S/N ratio of an output signal of the camera, which is a ratio between an amplitude of a detection signal for the normal texture and that for the defect, was so low that it was hard to discriminate between the normal portion and the defective portion. The present applicant also tried to detect coating unevenness of the film with the method of the above-mentioned Japanese Laid-open Patent Application No. 11-030591, where the polarizing direction of the polarizing plates was displaced not more than ±20° from the vertical direction to the film. However, it was found that the S/N ratio was worsened except where the displacement of the polarizing direction was zero degree, and the coating unevenness could hardly be detected even with the displacement of zero degree.

SUMMARY OF THE INVENTION

In view of the foregoing, a primary object of the present invention is to provide a detect inspection apparatus and a defect inspection method, which can detect defects of a film even if they are extremely fine.

To achieve the above object, the present invention suggests a defect inspection apparatus for detecting defects of a film while the film is being conveyed continuously in a transport direction, the apparatus comprises a light source for projecting light onto a surface of the film; a light receiver placed on an opposite side of the film to the light source, the light receiver receiving light projected from the light source and transmitted through the film, to output photoelectric signal corresponding to the received light; and a judging device for judging based on the photoelectric signal from the light receiver as to whether there is a defect in the film or not, wherein the light receiver is positioned to satisfy the following conditions:

$$30° \leq \theta1 \leq 50°, -60° \leq \theta2 \leq +60°$$

wherein $\theta1$ represents an angle formed between an optical axis of the light receiver and a normal line that is perpendicular to the surface of the film, and $\theta2$ represents a rotational angle of the optical axis to the transport direction, as rotated about the normal line.

According to a preferred embodiment, the light receiver comprises a taking lens and a line image sensor having a large number of photo sensors arranged in a line, wherein the line of the photo sensors is inclined to a widthwise direction of the film. The widthwise direction is orthogonal to the transport direction.

It is preferable to displace a focal point of the taking lens from the surface of the film.

Where the film to inspect is a retardation film, it is preferable to provide the defect inspection apparatus with a first polarizing plate placed between the light source and the film, and a second polarizing plate placed between the light receiver and the film, wherein polarizing directions of the first and second polarizing plates cross orthogonally each other.

According to the present invention, a method of inspecting defects of a film comprises steps of projecting light onto a surface of the film while conveying the film continuously in a transport direction; receiving light projected onto and transmitted through the film by a light receiver, an optical axis of the light receiver being inclined to a normal line that is perpendicular to the surface of the film by an angle of 30° to 50°, and rotated about the normal line by an angle of −60° to +60° to the transport direction; and judging based on the light received on the light receiver, as to whether there is a defect in the film or not.

BRIEF DESCRIPTION OF THE DRAWINGS

The above and other objects and advantages will be more apparent from the following detailed description of the preferred embodiments when read in connection with the accompanied drawings, wherein like reference numerals designate like or corresponding parts throughout the several views, and wherein:

FIG. 8 is a graph illustrating a wave form of a photoelectric signal detecting a thickness defect, obtained according to a conventional inspection method.

DESCRIPTION OF THE PREFERRED EMBODIMENTS

Figure 1:
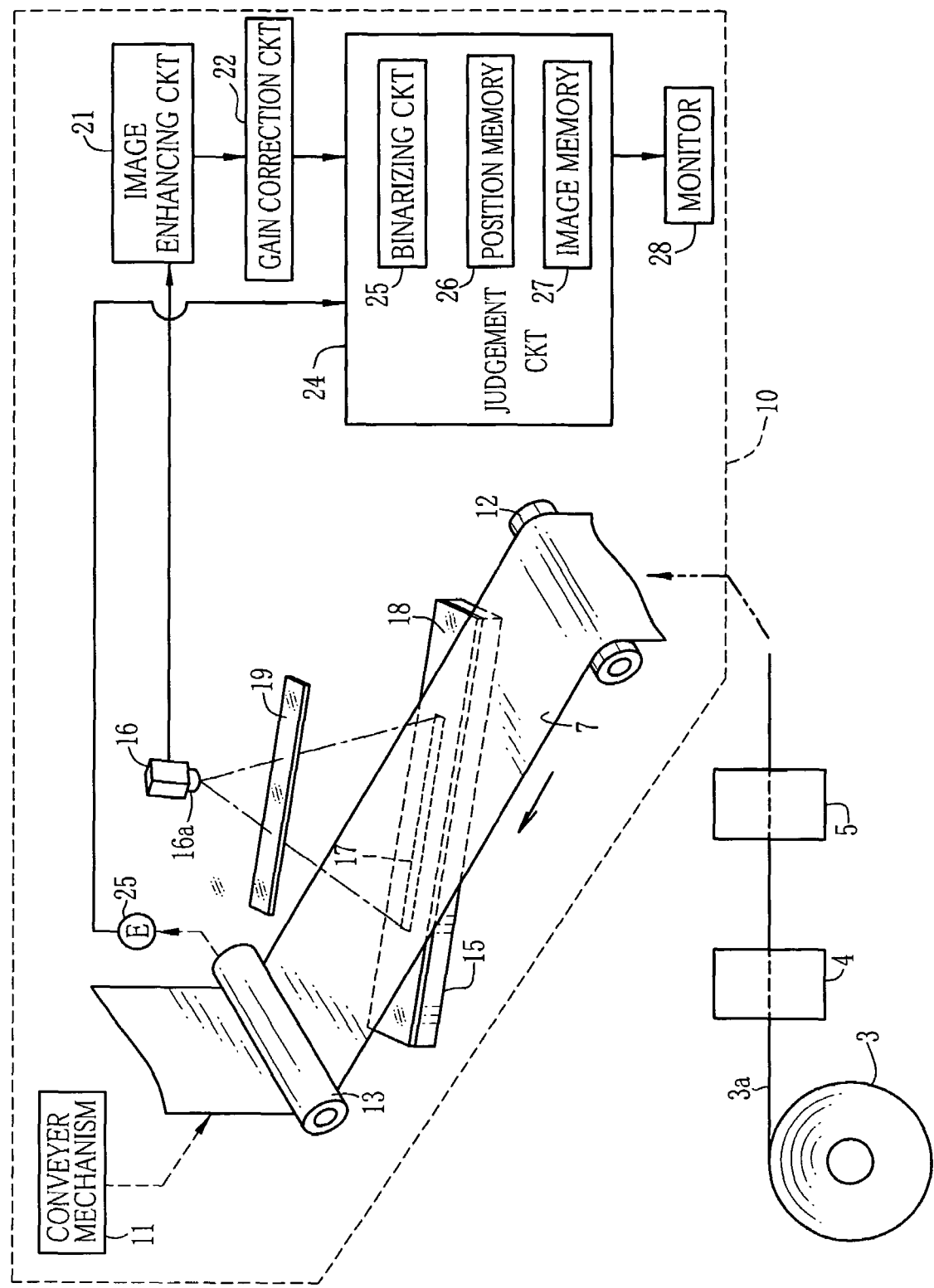
FIG. 1 is a schematic diagram illustrating a defect inspection apparatus according to an embodiment of the present invention.

In FIG. 1, a long web of transparent resin film 3a is fed out from a film roll 3, and is fed into an alignment layer forming device 4. The alignment layer forming device 4 spreads a coating liquid, which contains a resin for forming an alignment layer, on the film 3a, and dries the coating liquid by heating, to form a resin layer for the alignment layer. The resin layer on the transparent resin film 3a is processed into an alignment layer through a rubbing treatment. Thereafter, the film 3a is fed to a liquid crystal layer forming device 5

The liquid crystal layer forming device 5 spreads a coating liquid containing a liquid crystalline compound over the alignment layer of the transparent resin film 3a, evaporates a solvent of the coating liquid, and then heats the film 3a up to a liquid crystalline phase forming temperature, thereby to form a liquid crystal layer. Thereafter, ultraviolet rays are projected onto the liquid crystal layer to bridge it. In this way, the transparent resin film is provided with the liquid crystal layer, to manufacture a transparent retardation film. The retardation film is utilized as a transmitting optical compensation film for improving viewing angle of a liquid crystal display device.

A defect inspection apparatus 10 of the present invention is used for inspecting a film sheet 7, including the retardation film manufactured in the way as above. The film sheet 7 to inspect may be an antireflective coating film or other kind of transparent or translucent film.

The defect inspection apparatus 10 is designed to detect any defects, including uneven thickness, uneven coating and irregular molecular orientation. As for the thickness defect and the coating defect, the defect inspection apparatus 10 can detect a defect whose thickness difference is 1 nm to 1 μm and whose width is 0.1 mm to 50 mm.

The defect inspection apparatus 10 transports the film 7 in a single direction through a conveyer mechanism 11. A couple of guide rollers 12 and 13 are placed at a given interval on a transport path of the film 7, and the film 7 is turned around the guide rollers 12 and 13. The guide rollers 12 and 13 can idly rotate, so they rotate along with the movement of the film 7. As being turned around the guide rollers 12 and 13, the film 7 is kept flat in an inspection stage between the guide rollers 12 and 13. In the inspection stage, the liquid crystal layer of the film 7 is oriented downward.

A light source 15 and a light receiver 16 are placed in the inspection stage. The light source 15 is placed below the transport path, i.e. on the side of the liquid crystal layer of the film 7, so as to project light toward the liquid crystal layer, i.e. the bottom side of the film 7. The light source 15 converts light of a halogen lamp of 100 W to 200 W or the like, to a linear light through a quartz light guide or a plastic light guide, and projects the linear light toward an inspection area 17. As described in detail later, the light source 15 is inclined to a widthwise direction of the film 7, so is the inspection area 17.

The light receiver 16 is placed above the transport path, i.e. above the film 7. The light receiver 16 is constituted of a linear array camera, which has a taking lens 16a and a not-shown line image sensor consisting of a large number of photo sensors arranged in a line. The light receiver 16 takes an image of the film 7 at the linear inspection area 17 as photoelectric signal, each time the film 7 is conveyed by a constant length. The light receiver 16 converts the optical image into a photoelectric signal. In other words, the light receiver 16 receives a line of light that travels through the film 7 in the inspection area 17 after being projected from the light source 15, and photoelectrically converts the received light into the electric signal, and outputs the electric signal. Although the light source 15 is placed under the film 7, i.e. on the side of the liquid crystal layer, it is possible to place the light receiver 16 on the side of the liquid crystal layer, while placing the light source 15 on the opposite side from the liquid crystal layer.

In the present embodiment, the taking lens 16a is a zoom lens, so the distance between the light receiver 16 and the film 7 is adjusted to set the inspection area 17 at a given length, e.g. 250 mm. Since the film 7 to inspect is the retardation film that is dependent on the viewing angle, the distance between the light receiver 16 and the film 7 is made so large that the dependency on the viewing angle has little influence on the defect inspection. In this embodiment, the distance between the light receiver 16 and the film 7 is 1.5 m. The focal point of the taking lens 16a is displaced a little forward or rearward from the top surface of the film 7. The amount of displacement of the focal point is determined to be optimum by experiments and the like.

A first polarizing plate 18 is placed between the light source 15 and the film 7, whereas a second polarizing plate 19 is placed between the film 7 and the light receiver 16. So the light from the light source 15 is projected through the first polarizing plate 18 onto the film 7, and the light receiver 16 receives the light that travels through the second polarizing plate 19.

In this embodiment, the polarizing direction of the first polarizing plate 18 and that of the second polarizing plate 19 are determined to be crossed nicols, in order to detect the defect of the retardation film. But the polarizing directions of the first polarizing plate 18 and the second polarizing plate 19 to the film 7 may be modified appropriately depending upon what kind of film is to inspect. It is also possible for some kind of film, to place only one of the first and second polarizing plates, or neither of the polarizing plates. For example, if the film 7 to inspect is an antireflective coating film, placing no polarizing plate can be preferable.

A photoelectric signal from the light receiver 16 is sent to an image enhancing circuit 21, which processes the photoelectric signal to enhance those portions of the signal which correspond to defects of the film 7. Besides the image enhancement, it is possible to carry out noise reduction for reducing low and high frequency noise components, spatial frequency filtering for enhancing luminance variations, or shading compensation for compensating for darkening in the edge of the taking lens 16a.

A gain correction circuit 22 corrects the gain of the photoelectric signal output from the image enhancing circuit 21, so as to make the photoelectric signal have a proper signal level. The gain correction circuit 22 outputs the photoelectric signal to a judgment section 24.

The above-mentioned guide roller 13 is mounted with an encoder 25. The encoder 25 generates an encode pulse signal each time the guide roller 13 has rotated a given angle, that is, each time the film 7 has been conveyed by a given length. The encode pulse signal is sent to the judgment section 24.

The judgment section 24 is provided with a binarizing circuit 25 that binarizes the photoelectric signal using a given threshold, to judge based on the binarized photoelectric signal as to whether the film 7 has a defect or not. When an uneven thickness or thickness defect is detected, the judgment section 24 memorizes position data of the defect in a position memory 26. The position data indicates a location of the defect in a lengthwise direction of the film 7 and a location of the defect in a widthwise direction of the film 7. Simultaneously, the photoelectric signal of one line that includes the defect and the photoelectric signal of several lines around the line including the defect are memorized in an image memory 27. The defect position data is calculated based on the encode pulse signal from the encoder 25, and a signal position in the photoelectric signal of one line, corresponding to the defective position. A monitor 28 displays the position data as memorized in the position memory 26 and an image produced from the photoelectric signal of the several lines as memorized in the image memory 27.

Figure 2:
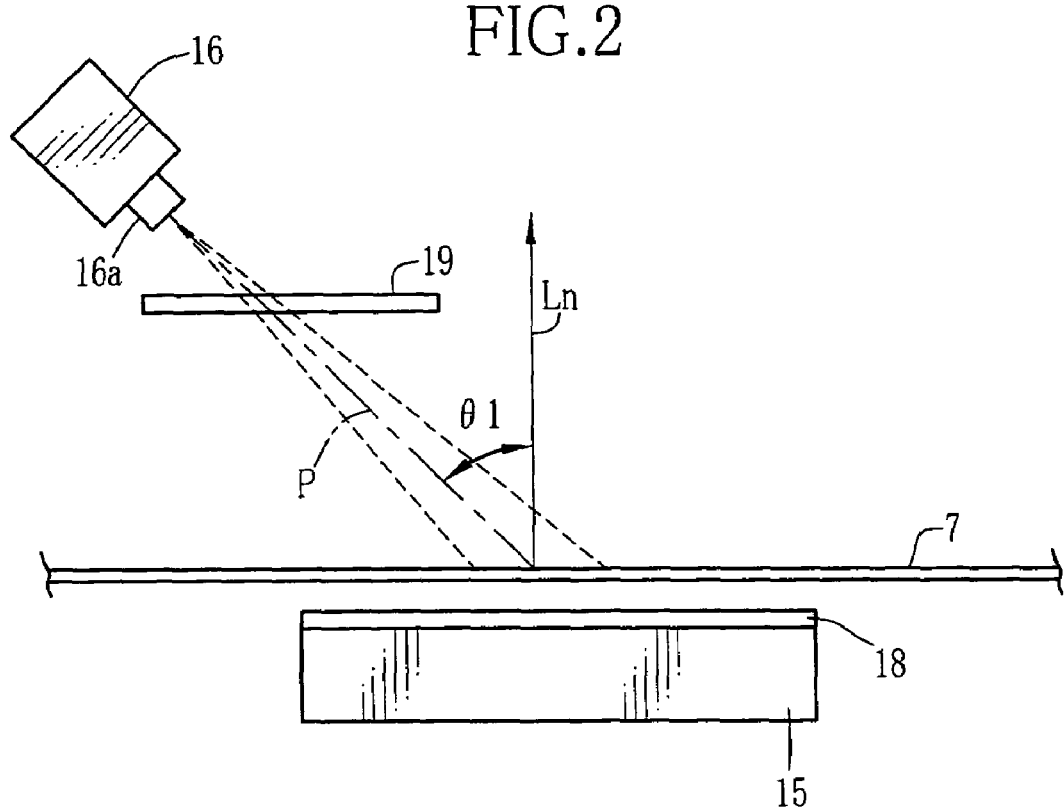
FIG. 2 is an explanatory diagram illustrating a cross angle θ1 of a light receiver.
Figure 3:
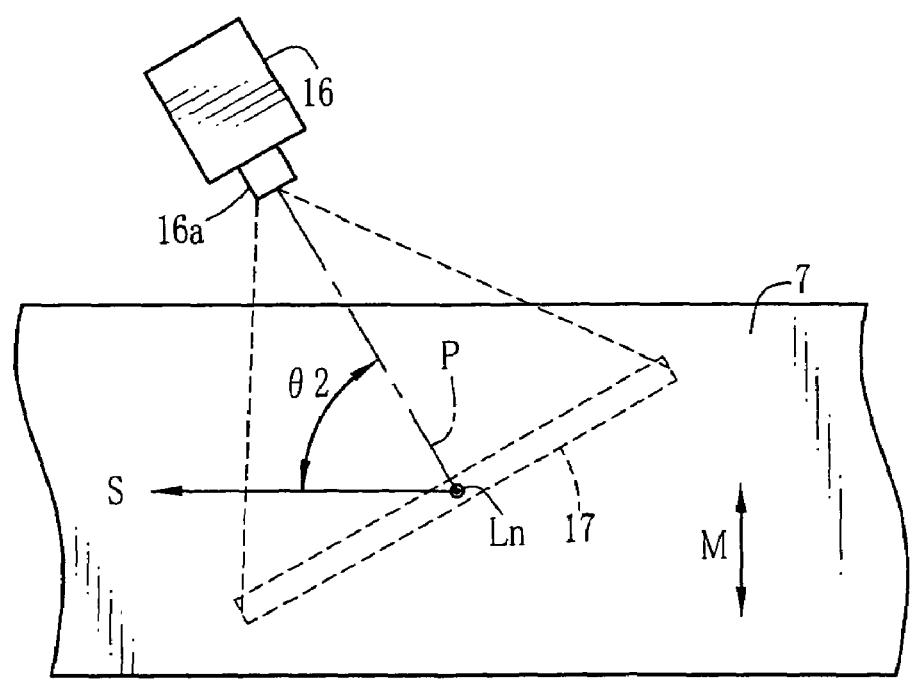
FIG. 3 is an explanatory diagram illustrating a rotational angle θ2 of the light receiver.

FIGS. 2 and 3 schematically show the position of the light receiver 16 relative to the film 7. As shown in FIG. 2, the light receiver 16 is placed to look down the film 7, with its optical axis P inclined by an angle $\theta 1$ to a normal line Ln that is perpendicular to the film surface. Hereinafter, the angle $\theta 1$ will be called the cross angle. Inclining by the cross angle $\theta 1$ to the normal line Ln has an effect of raising or improving S/N ratio that is a ratio of an amplitude level of the photoelectric signal as detecting the normal texture of the film 7 to an amplitude level of the photoelectric signal as detecting the defect. However, making the cross angle $\theta 1$ too large leads to lowering the S/N ratio. So it is preferable to set the cross angle $\theta 1$ in a range from 30° to 50°.

As shown from above in FIG. 3, the light receiver 16 is placed at a position turned about the normal line Ln by an angle $\theta 2$ to the transport direction S of the film 7. The angle $\theta 2$ will be called the rotational angle $\theta 2$, and has the same effect of improving the S/N ratio as the cross angle $\theta 1$, though the degree of improvement is smaller than that obtained by the cross angle $\theta 1$. Like the cross angle $\theta 1$, however, too large rotational angle $\theta 2$ lowers the S/N ratio. So it is preferable to set the rotational angle $\theta 2$ in a range from minus 60° to plus 60°, on the assumption that the transport direction S is zero degree, and the positive angle indicates the angle in the clockwise direction as viewed from above the film 7, and the negative angle indicates the angle in the counterclockwise direction. Note that the polarizing plates 18 and 19 are omitted from FIG. 3, for clarity sake.

Since the optical axis P of the light receiver 16 is rotated by the rotational angle $\theta 2$ to the transport direction S, the linear inspection area 17 of the light receiver 16 on the film 7 is inclined by the rotational angle $\theta 2$ to the widthwise direction M of the film 7. As being inclined in this way, the inspection area 17 is determined to have a length enough to cover a necessary range across the film 7 for the inspection.

As set forth in detail later, the above-described arrangement of the light receiver 16 makes it possible to detect such a fine defect as a thickness variation of 1 nm deep or so.

Now the operation of the defect inspection apparatus will be described.

The film 7 to inspect, the retardation film manufactured through the devices 4 and 5 in this embodiment, is sent to the inspection apparatus 10, and is conveyed one way through the inspection stage. While the film 7 is being conveyed, the light source 15 projects light through the first polarizing plate 18 onto the film 7, so the light receiver 16 takes a line of image each time the film 7 has been conveyed by the given length.

Every line of image as taken by the light receiver 16 is output as photoelectric signal of one line, and is sent through the image enhancing circuit 21 and the gain correction circuit 22 to the judgment section 24. The judgment section 24 judges based on the binarized photoelectric signal of each line, as to whether there is any defect, such as uneven thickness, uneven coating and irregular molecular orientation.

If there is a thickness defect, the photoelectric signal has a higher value at the defective portion of the film 7 than normal. So the judgment section 24 judges the higher signal as a defect, and writes position data of the defect in the lengthwise and widthwise directions of the film 7 onto the position memory 26. Simultaneously, the photoelectric signal of the line having the defect and ones of several lines before and after that line are written on the image memory 27, and the position data and an image showing the thickness defect are displayed on the monitor 28.

Since the defect is judged based on the photoelectric signal obtained from the film 7 by the light receiver 16 that is position with the above-mentioned cross and rotational angles $\theta 1$ and $\theta 2$, it becomes possible to detect the defects, including uneven thickness, uneven coating and irregular molecular orientation, even though they are very fine.

EXAMPLES

Experiments were made to prove the effects of the defect inspection apparatus 10 as configured above.

Example 1

Figure 4:
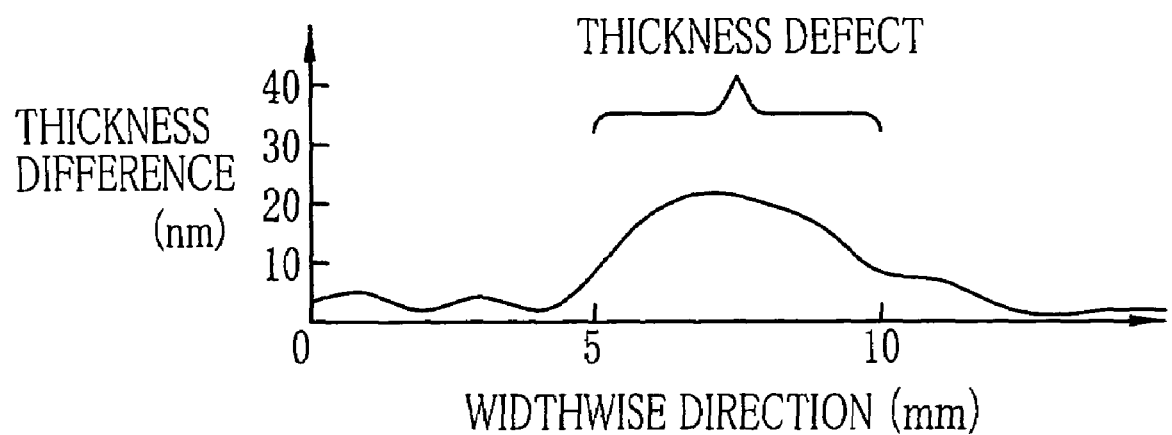
FIG. 4 is a graph illustrating a thickness curve showing a thickness defect.

As a sample, a portion having a coating defect in the liquid crystal layer was picked up from a retardation film that is used as a transparent optical compensation film. The coating defect of the sample was a protuberance of about 5 mm wide and has a thickness difference of about 20 nm from a normal portion of the film, as shown in FIG. 4.

In the example 1, the detection for the defect or uneven coating was tried a number of times while changing the cross angle θ1 and/or the rotational angle θ2, and the evaluation was made based on the S/N ratio of the photoelectric signal as enhanced through the image enhancing circuit 21. The S/N ratio is a ratio between an amplitude of a detection signal for the normal texture of the film and that for the defect. The S/N ratios obtained with the different cross and rotational angles θ1 and θ2 are shown in Table 1. Note that minus and plus of the rotational angle θ2 indicate the counterclockwise direction and the clockwise direction respectively to a film transport direction (0°) as viewed from above the retardation film, i.e. from the opposite side to the liquid crystal layer of the film.

TABLE 1

| | | ROTATIONAL ANGLE θ2(°) | | | | | | | |
|---|---|---|---|---|---|---|---|---|---|
| | | −75 | −65 | −45 | −30 | +30 | +45 | +65 | +75 |
| CROSS | 20 | 0.3 | 0.2 | 0.2 | 0.2 | 0.1 | 0.1 | 0.2 | 0.1 |
| ANGLE | 30 | 0.7 | 1.3 | 1.1 | 1.3 | 1.0 | 1.5 | 1.0 | 0.2 |
| θ1(°) | 40 | 0.8 | 1.2 | 1.7 | 0.8 | 1.0 | 0.9 | 1.2 | 0.4 |
| | 45 | 0.2 | 0.6 | 1.0 | 0.7 | 0.6 | 1.0 | 1.0 | 0.7 |
| | 50 | 0.1 | 0.4 | 0.6 | 0.4 | 0.5 | 0.8 | 0.9 | 0.5 |
| | 60 | 0.0 | 0.1 | 0.2 | 0.1 | 0.3 | 0.2 | 0.2 | 0.1 |

With an increase in the cross angle θ1, the S/N ratio increases, but it decreases with the cross angle θ1 as it goes above 40° or so. Because the S/N ratio does not go down to an impractical level right after the cross angle θ1 goes above 40°, the cross angle θ1 should be most preferably around 40°. In relation to the rotational angle θ2, it was found that the S/N ratio got higher as the absolute value of the rotational angle θ2 increases, and the S/N ratio became the highest around the rotational angles of minus 45° and plus 60°, although the effect was not so remarkable as compared to the cross angle θ2.

According to the Example 1, where the cross angle θ1 was in a range from 30° to 50° and the rotational angle θ2 was in a range from minus 60° to plus 60°, the S/N ratio was adequate, and the coating defect was detected with sufficient accuracy on an on-line inspection.

Figure 5:
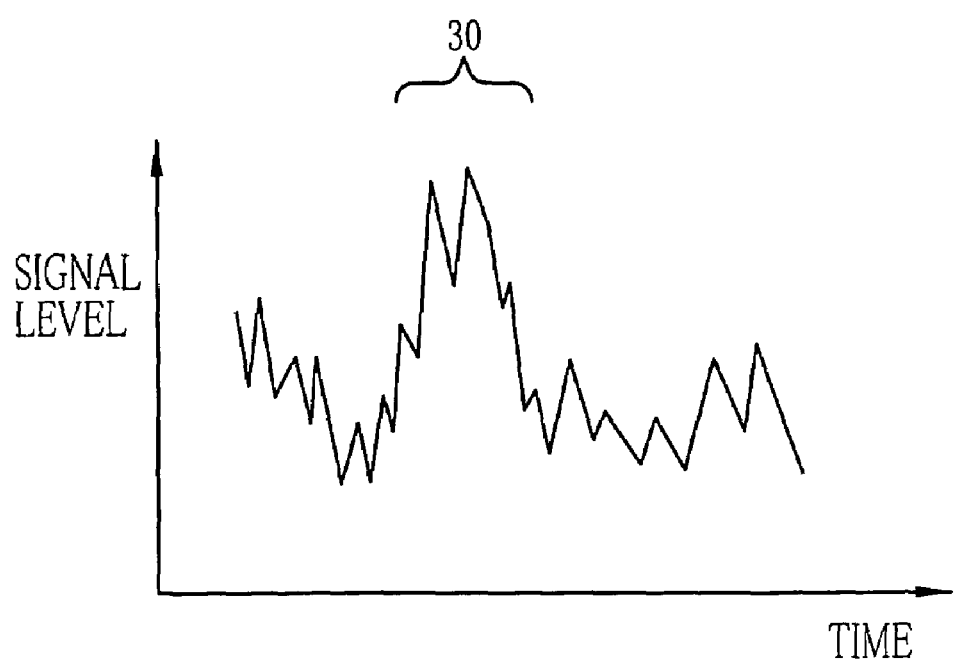
FIG. 5 is a graph illustrating a wave form of a photoelectric signal detecting a thickness defect, obtained by the defect inspection apparatus of the present invention.

FIG. 5 shows a wave form of the photoelectric signal detecting the above coating defect, as enhanced through the image enhancing circuit 21. A portion designated by a reference numeral 30 corresponds to the coating defect, and other portions correspond to the normal portion of the film. As seen from this wave form, the signal level is definitely higher in the portion 30 than in the normal portion, and the amplitude of the photoelectric signal resulted from the texture of the film is so small, that the defect is detectable without fail.

As a comparative, the same sample with the same coating defect was inspected while setting the cross and rotational angles θ1 and θ2 at zero degree. FIG. 8 shows a wave form of a photoelectric signal obtained in this comparative, wherein a portion designated by a reference numeral 31 corresponds to the coating defect. As shown in this comparative, the signal level of the photoelectric signal was not so different in the portion 31 from other portions, and the amplitude of the photoelectric signal resulted from the texture of the film was so large, that it was hard to detect the defect correctly.

Example 2

Figure 6:
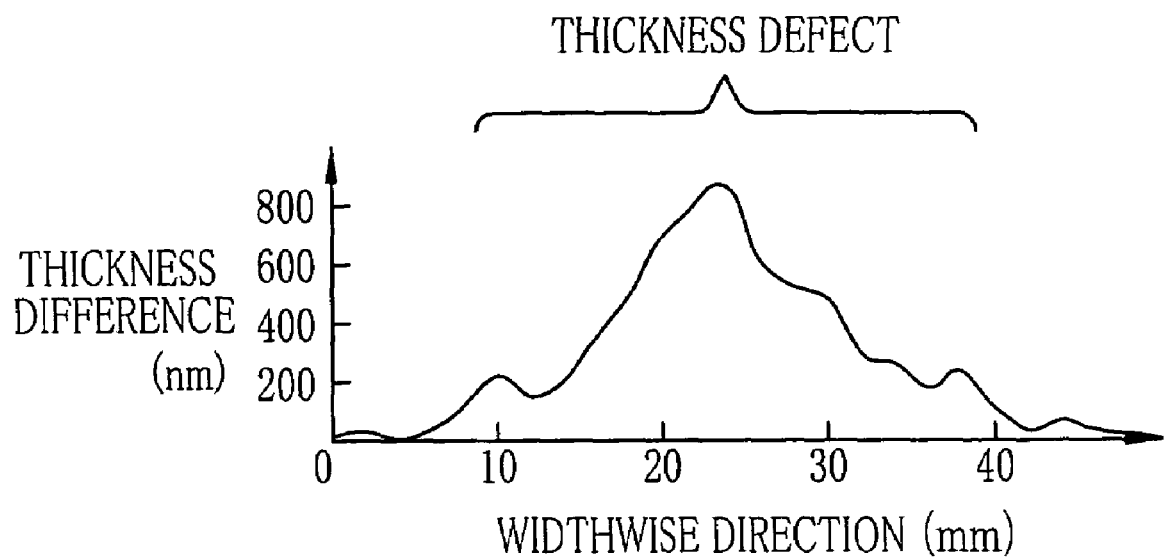
FIG. 6 is a graph illustrating a thickness curve showing a comparatively large thickness defect.

In the second example, a sample with a different coating defect was inspected by the defect inspection apparatus 10 as configured above. The sample in the second example was a portion having the coating defect of a retardation film used as a transparent optical compensation film, like in the first example. The coating defect of the second example was a protuberance of about 30 mm wide and has a thickness difference of about 800 nm from a normal portion of the film, as shown in FIG. 6.

The sample was inspected while changing the cross and rotational angles θ1 and θ2 in the same way as in the first example, and it was found that the S/N ratio of the photoelectric signal varied with the cross and rotational angles θ1 and θ2 in the same way as in the first example. Although the thickness difference of the defect was about 800 nm in the second example, which was certainly greater than the thickness difference of the defect in the first example, the S/N ratio was adequate where the cross angle θ1 was in a range from 30° to 50°, and the rotational angle θ2 was in a range from minus 60° to plus 60°, like in the first example. So the coating defect was detected with sufficient accuracy in this arrangement.

Example 3

Figure 7:
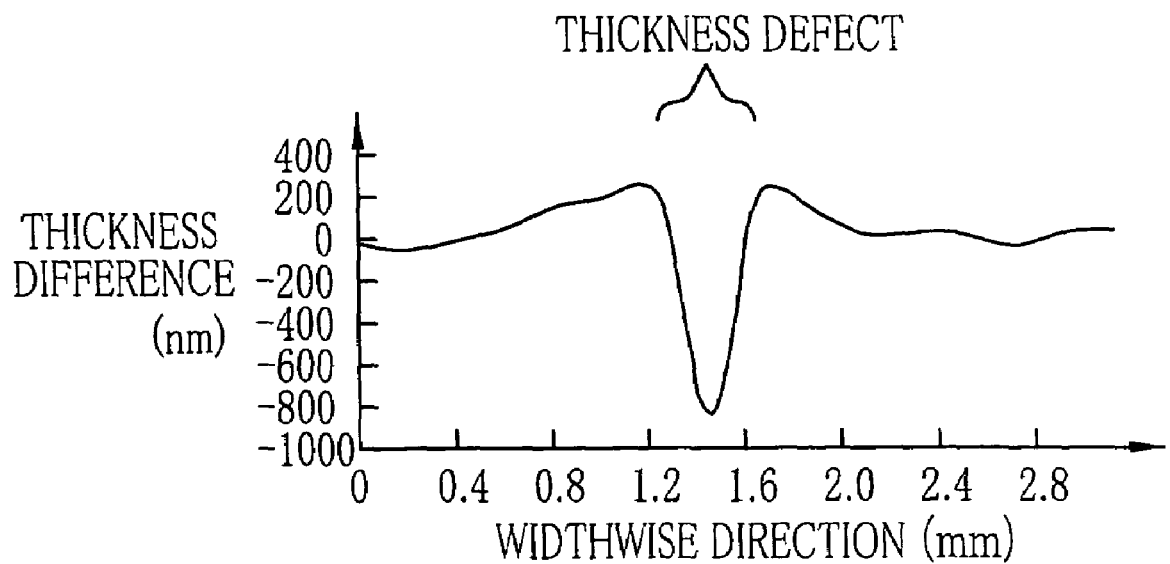
FIG. 7 is a graph illustrating a thickness curve showing a thickness defect where a liquid crystal layer is very thin.

In the third example, a sample with a coating defect of an extremely reduced thickness was inspected. The sample was a portion having the coating defect and picked up from a retardation film used as a transparent optical compensation film, like in the first example. The coating defect to detect in the third example was so-called repellent defect where the thickness was extremely reduced from a normal value since the coating liquid containing the liquid crystalline compound was repelled there when it was spread over the alignment layer. As shown in FIG. 7, the repellant defect to detect in the third example has a thickness difference of about 1000 nm from a normal portion, and a width of about 0.2 mm.

The sample was inspected while changing the cross and rotational angles θ1 and θ2 in the same way as in the first example, and it was found that the S/N ratio of the photoelectric signal varied with the cross and rotational angles θ1 and θ2 in the same way as in the first example. Accordingly, the coating defect with such a steep thickness variation was detected with sufficient accuracy when the cross and rotational angles θ1 and θ2 satisfied the conditions: 30°≦θ1≦50°, −60°≦θ2≦+60°.

Although the present invention has been described with reference to the preferred embodiments, the present invention is not to be limited to the above embodiments, but various modifications will be possible without departing from the scope of claims as appended hereto.

What is claimed is:

1. A defect inspection apparatus for detecting defects of a retardation film while said film is being conveyed continuously in a transport direction, said apparatus comprising:

a light source for projecting light onto a surface of said film;

a light receiver placed on an opposite side of said film to said light source, said light receiver receiving light projected from said light source and transmitted through said film, to output photoelectric signal corresponding to the received light; and a judging device for judging based on the photoelectric signal from said light receiver as to whether there is a defect in said film or not, wherein said light receiver is positioned to satisfy the following conditions:

$$30° \leq \theta1 \leq 50°, -60° \leq \theta2 \leq +60°$$

wherein $\theta1$ represents an angle formed between an optical axis of said light receiver and a normal line that is perpendicular to the surface of said film, and $\theta2$ represents a rotational angle of said optical axis to said transport direction, as rotated about said normal line.

2. A defect inspection apparatus as claimed in claim 1, wherein said light receiver comprises a taking lens and a line image sensor having a large number of photo sensors arranged in a line, said line of said photo sensors being inclined to a widthwise direction of said film, said widthwise direction being orthogonal to said transport direction.

3. A defect inspection apparatus as claimed in claim 2, wherein a focal point of said taking lens is displaced from the surface of said film.

4. A defect inspection apparatus as claimed in claim 2, wherein said line of said photo sensors being inclined by the same angle as said rotational angle $\theta2$ to said widthwise direction of said film.

5. A defect inspection apparatus as claimed in claim 2, wherein said light source projects a linear light onto a linear inspection area of said film, said inspection area being inclined by the same angle as said rotational angle $\theta2$ to said widthwise direction of said film.

6. A defect inspection apparatus as claimed in claim 1, further comprising a first polarizing plate placed between said light source and said film, and a second polarizing plate placed between said light receiver and said film, wherein polarizing directions of said first and second polarizing plates cross orthogonally each other.

7. A defect inspection apparatus as claimed in claim 1, wherein said film is an antireflective coating film.

8. A method of inspecting defects of a retardation film comprising steps of:

projecting light onto a surface of said film while conveying said film continuously in a transport direction;

receiving light projected onto and transmitted through said film by a light receiver, an optical axis of said light receiver being inclined to a normal line that is perpendicular to the surface of said film by an angle of 30° to 50°, and rotated about said normal line by an angle of −60° to +60° to said transport direction; and judging based on the light received on said light receiver, as to whether there is a defect in said film or not.

* * * * *